(12) United States Patent
McLean et al.

(10) Patent No.: US 7,081,617 B2
(45) Date of Patent: Jul. 25, 2006

(54) GAS-PHASE PURIFICATION OF BIOMOLECULES BY ION MOBILITY FOR PATTERNING MICROARRAYS AND PROTEIN CRYSTAL GROWTH

(75) Inventors: John A. McLean, Bryan, TX (US); David H. Russell, College Station, TX (US); J. Albert Schultz, Houston, TX (US)

(73) Assignees: Ionwerks, Inc., Houston, TX (US); The Texas A&M University System, College Station, TX (US)

( * ) Notice: Subject to any disclaimer, the term of this patent is extended or adjusted under 35 U.S.C. 154(b) by 0 days.

(21) Appl. No.: 11/038,834

(22) Filed: Jan. 20, 2005

(65) Prior Publication Data

US 2005/0189485 A1    Sep. 1, 2005

Related U.S. Application Data

(60) Provisional application No. 60/538,484, filed on Jan. 20, 2004.

(51) Int. Cl.
*B01D 59/44* (2006.01)
*H01J 49/00* (2006.01)

(52) U.S. Cl. ................. 250/283; 250/283; 250/282
(58) Field of Classification Search ............. 250/283, 250/282
See application file for complete search history.

(56) References Cited

U.S. PATENT DOCUMENTS

| 6,750,448 B1* | 6/2004 | Turecek et al. ............ 250/281 |
| 6,924,479 B1* | 8/2005 | Blanchard .................. 250/287 |
| 2003/0226963 A1* | 12/2003 | Cooks et al. ............... 250/283 |

OTHER PUBLICATIONS

Bergmann et al, High-Molecular-Mass Multi-c-Heme Cytochromes from Mathylococcus capsulatus Bath, Feb. 1999, Journal of Bateriology, vol. 181, No. 3, p. 991-997.*
Bergmann, David J. et al.; High-Molecular-Mass Multi-c-Heme Cytochromes from Methylococccus capsulatus Bath; Journal of Bacteriology, Feb. 1999, p. 991-997, vol. 181, No. 3.

* cited by examiner

*Primary Examiner*—John R. Lee
*Assistant Examiner*—Jennifer Yantorno
(74) *Attorney, Agent, or Firm*—Fulbright & Jaworski LLP

(57) ABSTRACT

A method and device for the gas-phase separation of ionic biomolecules including peptide, and protein or inorganic cluster ions or nanoparticles by ion mobility and for depositing them intact on a surface in a spatially addressable manner is described. The surface onto which the proteins are deposited can be modified for the purpose of constructing microarrays of biologically relevant materials or for promoting the growth of highly ordered protein crystals.

27 Claims, 6 Drawing Sheets

(A)

(B)

GAS-PHASE PURIFICATION OF BIOMOLECULES BY ION MOBILITY FOR PATTERNING MICROARRAYS AND PROTEIN CRYSTAL GROWTH

CROSS-REFERENCE TO RELATED APPLICATIONS

This application claims priority to U.S. provisional application 60/538,484 filed on Jan. 20,2004.

TECHNICAL FIELD

The present invention relates to a method and device for the gas-phase separation of peptide and protein ions (or other biological molecules) by ion mobility and for depositing them intact on a surface in a spatially addressable manner. The surface onto which the proteins are deposited can be modified for the purpose of constructing microarrays of biologically relevant materials or for promoting the growth of highly ordered protein crystals.

BACKGROUND OF THE INVENTION

Analogous to DNA-based array techniques, protein microarrays based on antibody (fragments, mimics, or phage display), aptamer, or affinity ligand arrays have been developed for (i) rapid screening of protein expression, (ii) identification of protein-protein, protein-DNA, and protein-ligand interactions, and (iii) determination of post-translational modifications. However, techniques for constructing protein arrays, such as (i) photolithography, (ii) robotic spotting, (iii) droplet printing techniques, (iv) micro-contact printing, and (v) dip-pen nanolithography often lack selectivity for structural conformations of a particular protein or for protein modifications. It should be noted that all of these techniques require analyte purification prior to deposition on the surface substrate (e.g., spatially distinct protein spots to probe protein-protein interactions). Furthermore, solution-based methods (separation based on analyte hydrophobicity, affinity, isoelectric point, etc.), which are typically used for analyte purification, are usually time consuming and are inefficient at separating protein isoforms (conformational or structural). These drawbacks are particularly salient, for example, in developing assays for protein misfolding diseases (e.g., transmissible spongiform encephalopathies, amyloidoses, and prion diseases). The present invention is a gas-phase purification method for biological molecules based on ion mobility and methods for selectively depositing material in a spatially addressable manner onto a surface.

Gas-phase ion mobility (IM) provides ion separation by generating or injecting ions in/into a gas-filled drift tube (typically 1 to 760 Torr) where they migrate under the influence of a weak electrostatic-field (typically 10 to 100 V cm$^{-1}$ Torr$^{-1}$). The theory of IM is fully developed in texts by Mason and McDaniel, (E. W. McDaniel and E. A. Mason, "The Mobility and Diffusion of Ions in Gases", Wiley, New York, N.Y. (1973); E. A. Mason and E. W. McDaniel, "Transport Properties of Ions in Gases", John Wiley & Sons, Inc., New York, N.Y. (1988)) and the combination of IM with mass spectrometry dates back to the early 1960's. (see *Phys. Rev. Lett.* 6, 110–111 (1961)). Briefly, the mobility (K) of an ion is defined as the ratio of the drift velocity ($v_d$) to the electric field strength (E):

$$K = \frac{v_d}{E} \quad (1)$$

When the ion-neutral collision energy approaches the thermal energy of the system, the mobility approaches the so-called "low-field" limit and can be related to the collision cross-section ($\Omega$), or apparent surface area, of the ion:

$$K = \frac{3}{16} \frac{q}{N} \left( \frac{1}{\mu} \frac{2\pi}{k_B T} \right)^{\frac{1}{2}} \frac{1}{\Omega} \quad (2)$$

Where N is the number density of the drift gas, q is the ion charge, $\mu$ is the reduced mass of the ion-neutral collision pair, $k_b$ is Boltzmann's constant, and T is the system temperature. Thus, ion mobility provides separation selectivity based on the charge-to-collision cross-section ratio of the ion in a particular drift gas, in contrast with mass spectrometry based ion separation, which separates analyte on the mass-to-charge (m/z) ratio of the ion.

The mobility-separated ions elute from the IM drift cell with near-thermal kinetic energies, which provides unique potential for deposition onto a surface. The energy regime (e.g., thermal (<1 eV), hyperthermal (1–100 eV), low-energy (0.1–10 keV), or high energy (keV–MeV)) with which the ion collides with a surface dictates the prevailing ion-surface interaction that ensues. For example, when an intact ion or molecule comes to rest on a surface, i.e., with insufficient collisional energy to break the chemical bonds of the molecule, it is hereafter termed "soft-landing." Cooks has described the soft-landing energy regime to be in the range of typically 5–10 eV, but this is highly dependant on the identity of the ion and the surface onto which it is landed (see *Rev. Sci. Instrum.* 72, 3149–3179 (2001)). For example, larger molecules possess many more degrees-of-freedom (i.e., energy levels) into which collision energy can be deposited; consequently, large ions can dissipate the energy into ro-vibronic modes or transfer the energy to the surface (e.g., closely spaced alkyl chains comprising a self-assembled monolayer (SAM)). Note also that the extent of translational-to-internal energy conversion of the ion and the extent of the inelastic partitioning of energy between the ion and the surface strongly depends on the surface composition (ranging from ~60–70% energy transfer to the surface for SAMs). Similarly, neutralization of the impinging ion also depends on the ion type and surface composition. For example, electron transfer from the surface easily neutralizes odd-electron ions, but this reaction does not apply to even-electron ions. Further, neutralization is less efficient with F-SAM than H-SAM surfaces (fluorinated and protonated SAMs) where charge-exchange is more efficient with a hydrocarbon rather than fluorinated surface (reflected in the higher ionization potential of fluoroalkanes) (*Int. J. Mass Spectrom. Ion Proc.* 122, 181–217 (1992)). To afford the soft-landing of ions, prior art has consisted of selecting the ions to be landed by mass spectrometric methods. In contrast, soft-landing after ion mobility selection can be achieved without the need for elaborate deceleration lenses which are sometimes necessary to lower the collisional energy of the ion with the target surface.

In the late 1970's, Cooks and colleagues first demonstrated soft-landing of mass-to-charge selected $CS^{•+}$, $CS_2^{•+}$, and $CS_2^{2+}$ ions with various metal targets for surface modification (*Int. J. Mass Spectrom. Ion Phys.* 23, 29–35 (1977)). These researchers showed that impinging a $CS_2^{\cdot}$ beam onto a lead target at kinetic energies of 10 eV yielded sulfide species of more covalent character than those obtained using 1 keV ions (as indicated by a shift to higher binding energies as determined by X-ray photoelectron spectroscopy (XPS)). This indicated that surface chemical reaction with molecular ions was possible at low collision energies, whereas at 1 keV reactions were dominated by those of atomic species (i.e., the molecule likely dissociates into constituent atomic neutrals/ions prior to reaction with surface species). Subsequently, Rabalais and colleagues demonstrated the generation of metal carbides and the diamond allotrope of carbon (i.e., $sp^3$ hybridized carbon films) by impinging a mass-to-charge selected hyperthermal (20–200 eV) beam of $C^{\cdot+}$ onto several different metal surfaces (i.e., Si(100), Ni(111), Ta, W, and Au) (*Science* 239, 623–625 (1988)). In a related report, these researchers investigated the interaction of mass-to-charge selected low kinetic energy beams (3–300 eV) of $C^{\cdot+}$, $O^{\cdot+}$, and $CO^{\cdot+}$ with a Ni(111) surface (*J. Chem. Phys.* 88, 5882–5893 (1988)). It was found that $CO^{\cdot+}$ preferentially dissociated above a collisional kinetic energy of ca. 9 eV, whereas at lower energies the yield of intact (i.e., soft-landed) CO was significantly enhanced (determined by XPS and Auger electron spectroscopy). It was later demonstrated that larger polyatomic ions, such as silyl ethers (e.g., $(CH_3)_3SiOSi(CH_3)_2^+$, $^{35}ClCH_2(CH_3)_2SiOSi(CH_3)_2^+$, and $^{37}ClCH_2(CH_3)_2SiOSi(CH_3)_2^+$), could be mass selected and soft-landed at low collisional kinetic energies (5 to 10 eV) on F-SAM surfaces (see *Science* 275, 1447–1450 (1997); *Int. J. Mass Spectrom. Ion Proc.* 174, 193–217 (1998)). The F-SAM surface provided two primary benefits: (i) energy dissipation via the $C_{10}$ fluoroalkane chains, and (ii) a proposed entanglement of soft landed molecules within the framework of the F-SAM assembly (particularly for sterically bulky species). The utility of H-SAM surfaces ($C_{12}$) were also examined, which provide "softer" surfaces onto which ions can be landed in that the conversion of translational to internal energy of the ion is reduced in comparison with an F-SAM, ~13% vs. 20–30% for an H-SAM and an F-SAM, respectively (*Int. J. Mass Spectrom.* 182/183, 423–435 (1999) and references therein).

The soft-landing of biologically relevant molecules by using low-energy mass selected ions was recently described by Smith and coworkers. They used Fourier transform ion cyclotron resonance to mass-select and soft-land a 160 base pair double-stranded oligonucleotide onto a nitrocellulose membrane (*J. Am. Chem. Soc.* 121, 8961–8962 (1999)). Cooks and colleagues have more recently demonstrated selective soft-landing and subsequent bioactivity measurements of several proteins (cytochrome c, lysozyme, apomyoglobin, insulin, and trypsin) representing a complex mixture. In this work, a linear ion trap mass spectrometer was used where an estimated 80% soft landing efficiency (from trapped ions to plate deposition) was achieved with 2 mm spatial resolution (see (1) B. Gologan, Z. Takats, T. Blake, Z. Ouyang, V. J. Davisson, and R. G. Cooks, Self-Assembled Monolayers as Substrates for Laser Desorption: Analysis of Soft-Landed Proteins, presented at the 51st American Society for Mass Spectrometry Conference, Montreal, Canada, June 2003; (2) Z. Takats, Z. Ouyang, B. Gologan, T. Blake, A. J. Guymon, V. J. Davisson, and R. G. Cooks, Protein Microarrays by Ion Soft-Landing, presented at the 51st American Society for Mass Spectrometry Conference, Montreal, Canada, June 2003; and (3) T. A. Blake, Z. Ouyang, A. J. Guymon, S. Kothari, Z. Takats, B. Gologan, and R. G. Cooks, A Microarray Fabrication System Using Ion Soft-Landing from a Linear Ion Trap Mass Analyzer, presented at the 51st American Society for Mass Spectrometry Conference, Montreal, Canada, June 2003).

BRIEF SUMMARY OF THE INVENTION

In the present invention, there is an apparatus for detecting and selectively depositing gas-phase ions onto a surface, comprising: an ion source for generating ions; means for separating the generated ions, said means for separating being fluidly coupled to said ion source; means for selectively gating said ions based on their mobilities and means for directing said ions to a substrate, said means for selectively gating and said means for directing being fluidly coupled to said ion mobility drift cell; and, an ion detector fluidly coupled to said ion mobility drift cell. In some embodiments, the ion source is selected from the group consisting of atmospheric pressure MALDI, infrared MALDI, LDI, electrospray, nanospray, photoionization, multiphoton ionization, resonance ionization, thermal ionization, surface ionization, electric field ionization, chemical ionization, atmospheric pressure chemical ionization, radioactive ionization, discharge ionization, and any combination thereof. In some embodiments, the means for separating comprises an ion mobility cell or a mass spectrometer or both. In some embodiments, the means for separating comprises an ion mobility cell. In some embodiments, the ion mobility cell applies electric fields selected from the group consisting of uniform electrostatic fields, periodic-focusing electrostatic fields, and any combinations thereof. In some embodiments, the ions are further separated by unreactive and/or reactive collisions with species selected from the group consisting of helium, neon, argon, krypton, xenon, nitrogen, oxygen, methane, carbon dioxide, water, methanol, methyl fluoride, deuterated analogs thereof, tritiated analogs thereof, and any combination thereof. In some embodiments, the means for selectively gating ions based on their mobilities and directing them to a solid substrate comprises directing ions by a technique selected from the group consisting of direction by an electrostatic-field, direction by a magnetic-field, and a combination of direction by an electrostatic-field and direction by a magnetic-field. In some embodiments, the means for selectively gating and said means for directing are the same. In some embodiments, the means comprises an electrostatic steering plate. In some embodiments, the apparatus gates and directs ions to a solid or condensed-phase surface at energies of 0 to 10 eV. In some embodiments, the apparatus gates and directs ions to a solid or condensed-phase surface at energies of 10 to 100 eV. In some embodiments, the apparatus gates and directs ions to a solid or condensed-phase surface at energies of 100 to 1000 eV. In some embodiments, the apparatus gates and directs ions to spatially distinct regions of a surface comprising a material selected from the group consisting of steel, gold, glass, self-assembled monolayer(s), nitrocellulose, condensed-phase substrates, chemically functional moieties, chemically reactive moieties, biologically active species, and combinations, patterns and layers thereof. In some embodiments, the apparatus further comprises an RF cooling apparatus. In some embodiments, the apparatus further comprises deceleration optics upstream of said substrate. In some embodiments, there is an apparatus for detecting and selectively depositing gas-phase ions onto a surface, the apparatus comprising an ion source for generating ions, a two dimensional ion mobility spectrometer fluidly coupled to said ion source, means for directing said ions to a substrate, said means for directing being fluidly coupled to said ion mobility drift cell.

In another aspect of the present invention, there is a method for analyzing and selectively depositing gas phase ions comprising: generating ions from an ion source; separating said ions; detecting said ions; and, selectively gating and directing said ions onto a substrate. In some embodiments, the said step of selectively gating and directing comprises depositing said ions onto a substrate in a spatially addressable manner by patterning ions onto a solid substrate, patterning ions onto a condensed-phase substrate, or a combination of patterning ions onto a solid substrate and patterning ions onto a condensed-phase substrate. In some embodiments, the ions to be patterned comprise ions of species selected from the group consisting of amino acids, polyamino acids, nucleotides, polynucleotides, antibodies, antibody antigens, carbohydrates, polycarbohydrates, biomolecules, ligands, mimics, aptamers, derivatives thereof, assemblies thereof, complexes thereof, and any combination thereof. In some embodiments, the ions comprise proteins or peptides or both. In some embodiments, the ions comprise small molecules interacting with proteins or peptides or both proteins and peptides. In some embodiments, the step of directing promotes the growth of ordered crystals. In some embodiments, the ions to be patterned comprise ions with a molecular weight less than 100000 amu. In some embodiments, the ions to be patterned comprise ions with a molecular weight less than 10000 amu. In some embodiments, the ions to be patterned comprise ions with a molecular weight less than 1000 amu. In some embodiments, the ions to be patterned comprise atoms/molecules with a molecular weight less than 500 amu. In some embodiments, the ions to be patterned comprise ions with a molecular weight greater than 100000 amu.

The present invention differs from the prior art in that ion selectivity is accomplished on the basis of charge-to-collision cross-section rather than mass-to-charge. Ion selectivity based on ion mobility separation provides several important advantages over prior art solution-based purification or gas-based mass-to-charge selection of biological molecules: (i) in many cases isobaric and isoform species (e.g., structural and/or conformational isomers) can be separated, (ii) the separation mechanism does not rely on solution-phase physical properties (e.g., affinity, hydrophobicity, isoelectric point, etc.), (iii) ion mobility is amenable to a wide variety of molecular classes or complex mixtures thereof (e.g., proteins, lipids, oligonucleotides, carbohydrates, etc.), and (iv) in many cases it is sensitive and selective for post-translationally modified peptides (or proteins).

The present invention is directed towards devices and methods for the ionization, gas-phase separation/purification, and subsequent spatially addressable deposition/collection of biomolecules. This differs from the prior art in that it uses ion mobility as a means to separate gas-phase ions on the basis of their apparent charge-to-surface area ratio (e.g., collision cross-section with a neutral drift gas) rather than mass-to-charge. In an exemplary embodiment of the present invention, biomolecular ions are generated by matrix assisted laser desorption/ionization (MALDI), whereby the analyte is co-crystallized with ultraviolet (UV) absorbing molecules (typically organic acids). The analyte and matrix is subsequently irradiated with UV photons to ultimately produce biomolecular ions. It should be noted that with minor modification to the present apparatus, other ion sources can be used, for example: atmospheric pressure MALDI, infrared MALDI, LDI, electrospray, nanospray, photoionization, multiphoton ionization, resonance ionization, thermal ionization, surface ionization, electric field ionization, chemical ionization, atmospheric pressure chemical ionization, radioactive ionization, discharge ionization, and combinations thereof.

The gas-phase ions can either be generated at the entrance plane of the ion mobility cell, or subsequently injected into the mobility cell for separation. The ions migrate under the influence of a uniform or periodic-focusing electrostatic field, whereby their translational motion is impeded by collisions with neutral drift gas molecules (e.g., He, $N_2$, Ar, $H_2O$, etc.). Note that by using a reactive drift gas, the ion mobility cell can also be used to modify the original ion through the promotion of gas-phase ion chemistry (charge-exchange, H/D exchange, solvation, etc.) for subsequent deposition. In the exemplary embodiment, ions exit the mobility drift cell with near-thermal kinetic energy. The ions are then accelerated to a low kinetic energy (1–10 eV) above the thermal temperature of the system and electrostatic lenses collimate and focus the ion beam. The ion beam then passes between two electrostatic steering plates whereby the temporal voltage state of the two plates determines the ultimate position where the selected ions will be deposited. For example, in the exemplary embodiment, ions are selected on the basis of their arrival time distribution in the region between the two steering plates. The state of the steering plates is switched to direct the selected ions to a collection surface and then switched (in a bracketed manner about the arrival time distribution of the selected ions) to direct non-selected ions towards an ion detector. The latter is performed to continuously monitor the arrival time distribution of the ensemble of ions generated by the ionization event.

The exemplary embodiment of the present invention, as described herein, provides for biomolecule ionization, gas-phase separation on the basis of ion mobility, ion selection, and spatially addressable ion collection/detection. A device (apparatus) has been constructed, according to the exemplary embodiment described herein, and utilized for the selective deposition of intact peptides. Modifications to the exemplary embodiment described herein are envisioned including the utilization of alternate ionization sources (described above), ion selection (optimization of ion optical geometries), ion collection (utilization of different energy regimes and surface modification(s)), and ion detection (mass spectrometry, fluorescence, condensation counting by Fraunhofer diffraction, etc.) strategies.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

As used herein, "a" or "an" means one or more. The plural encompasses the singular and the singular encompasses the plural.

The invention includes an instrument and method for detecting and selectively depositing gas-phase ions onto a surface. The instrument comprises an ion source for generating ions, means for separating the generated ions wherein the means for separating is fluidly coupled to said ion source; means for selectively gating said ions based on their mobilities and means for directing said ions to a substrate, said means for selectively gating and said means for directing being fluidly coupled to said ion mobility drift cell; and, an ion detector fluidly coupled to said ion mobility drift cell.

Figure 1:
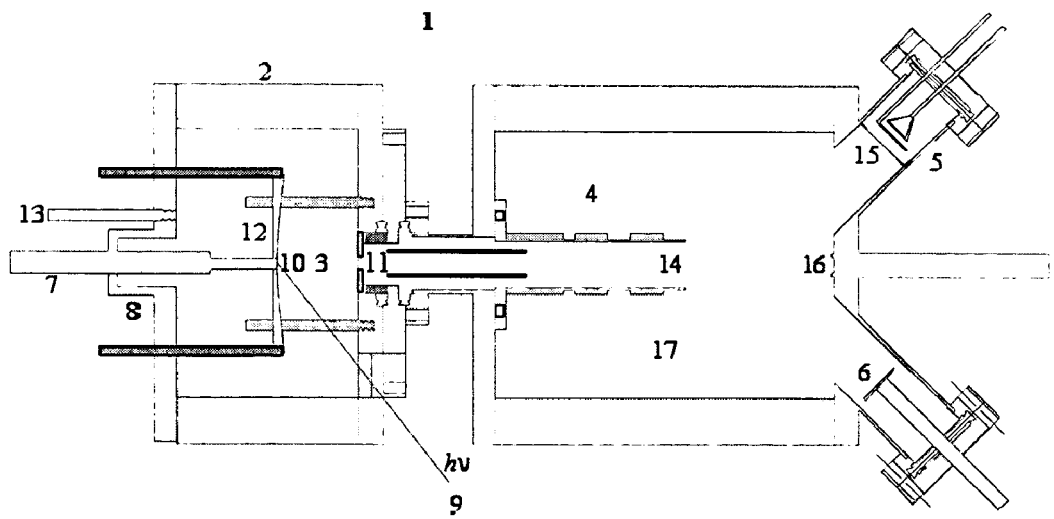
FIG. 1 is a (A) Schematic diagram of an exemplary embodiment of the present invention providing for ion mobility separation, ion optic selection, and subsequent soft-landing of ions, incorporating a multichannel plate ion detector. (B) Schematic diagram of an embodiment of the invention utilizing ion mobility separation, ion optic selection, and subsequent soft-landing of ions incorporating ion fluorescence detection.
Figure 1:
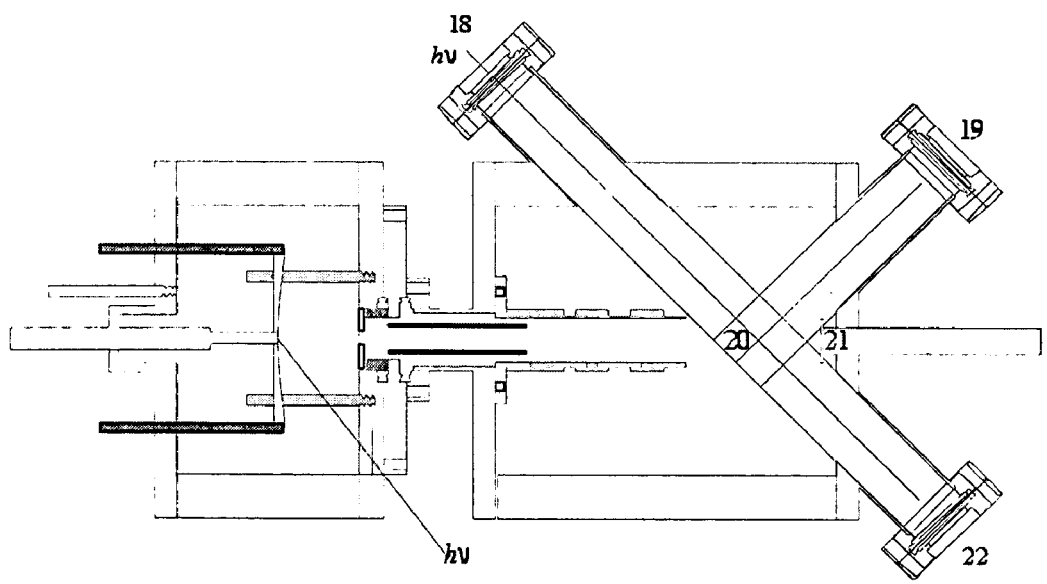

FIG. 1A provides a schematic diagram of a device representing an exemplary embodiment of the present invention, instrument 1, is comprised of five major components: an ion mobility chamber 2, a source of ions 3 (such as peptide and proteins), a system of ion lenses for focusing and beam positioning 4, a detector for determining ion mobility distributions 5, and a surface for means of collecting peptide or protein ions 6. Briefly, a solid matrix/protein sample is deposited on a probe 7 and subsequently introduced into the ion mobility chamber via a vacuum interlock 8. Ultraviolet photons from a laser 9 directed at the probe tip 10 then preferentially generates intact gas-phase protonated molecular ions which are directed towards a differential aperture plate 11 by means of applying a nearly-linear electric field between 11 and the ion mobility backing plate 12. A neural drift gas supplied to the ion mobility chamber via a metered port 13 impedes the progress of ions through the electric field. Provided a suitable ratio of the electric field to the neutral gas number density is used, ions are nearly linearly separated based on their apparent charge-to-collision-cross section ratio.

Figure 2:
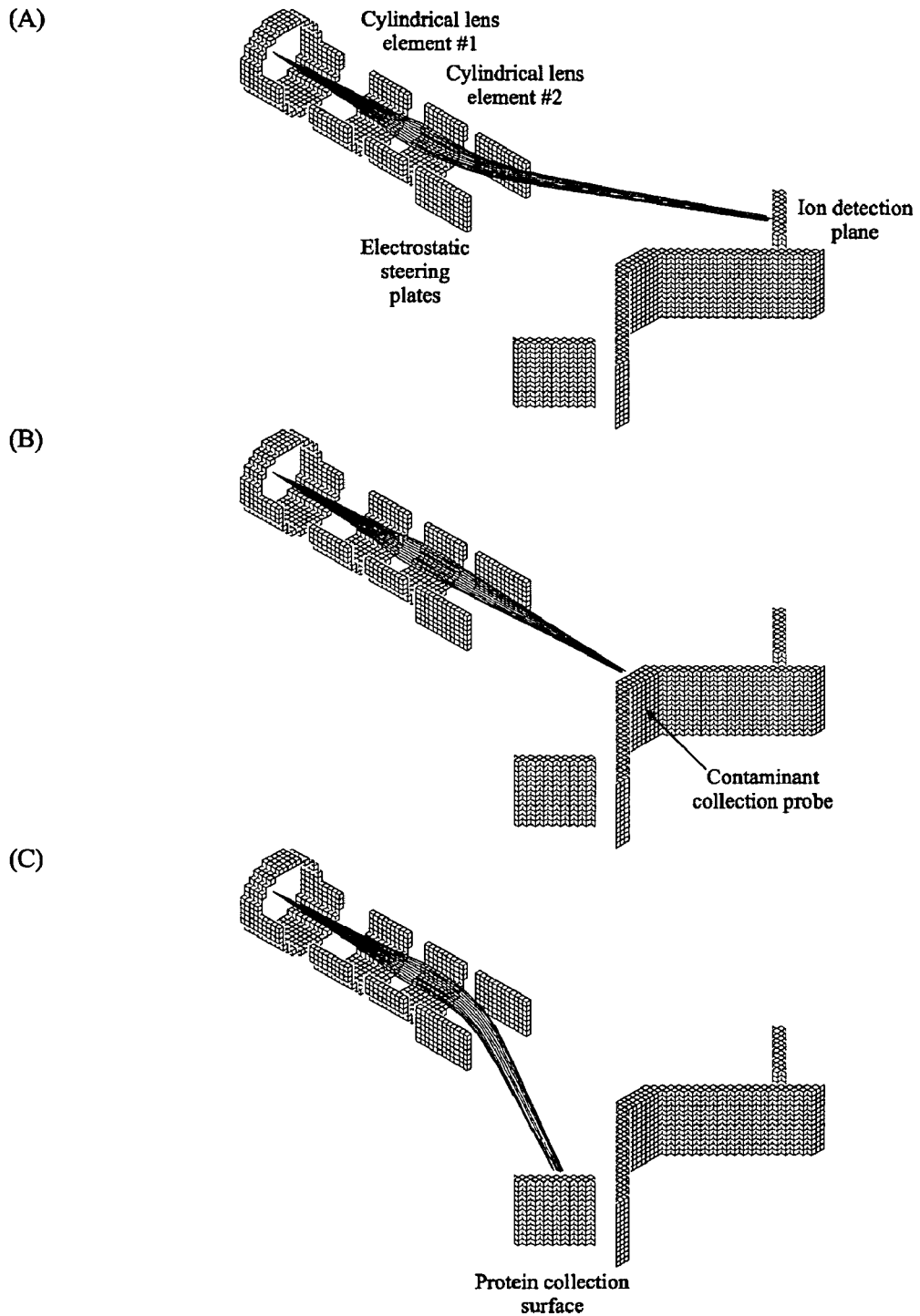
FIG. 2 is a Simulation of the ion trajectories of the invention allowing: (A) protein ion detection, (B) collection of undesired components of initial mixture, and (C) collection of the purified protein. Simulations were performed for 10 eV lysozyme (Hen egg white, M. W.=16,238 Da.) ions.

The separated peptide and protein ions then pass through the differential aperture plate 11 (200 to 1000 μm diameter) and are collimated and focused by a system of ion lens elements 4. In an exemplary embodiment of the present invention, the separated ions are then directed by electrostatic steering plates 14 to one of three final positions: an ion detector 15 (see also FIG. 2A), a contaminant collection probe 16 (see also FIG. 2B), or a peptide/protein collection surface 6 (see also FIG. 2C). When the separated ions are directed to the ion detector (FIG. 2A), the ion mobility distribution of all of the separated ions is recorded. Neutral atoms or molecules that pass through the aperture plate are not electrostatically steered from their straight trajectory and are collected on the contaminant collection probe or are pumped from the detector/collector cell 17. Based on the arrival time distribution of the ions that is recorded at the detector, a timing sequence for the voltages applied to the electrostatic steering plates for the selection of a particular peptide or protein for deposition is generated.

In the present invention, the ion source can be any ion source known in the art. Preferably, the ion source comprises by any ionization instrumentation, including but not limited, to atmospheric pressure matrix-assisted laser desorption ionization (MALDI), infrared MALDI, laser desorption ionization (LDI), electrospray ionization, nanospray ionization, photoionization, multiphoton ionization, resonance ionization, thermal ionization, surface ionization, electric field ionization, chemical ionization, atmospheric pressure chemical ionization, radioactive ionization, discharge ionization, and combinations thereof. Employing the ionization instrumentation on a sample generates ions. The sample can be any sample, but is preferably a chemical or biochemical sample. Means for separating ions can be accomplished by any means known in the art, but is preferably performed on the basis of the ions' gas-phase mobility (ion mobility). Preferably, when using ion mobility, the separating means comprises applying electric fields to the ions, and preferably, the electric fields are is selected from the group consisting of uniform electrostatic fields, periodic-focusing electrostatic fields, and combinations thereof. Other fields, known to those of skill in the art, are also useful in the present invention. Separation of ions on the basis of their gas-phase mobility is also accomplished by reactive or unreactive collisions with species selected from the group consisting of helium, neon, argon, krypton, xenon, nitrogen, oxygen, methane, carbon dioxide, water, methanol, methyl fluoride, deuterated analogs thereof, tritiated analogs thereof, and any combinations thereof. Means for selectively gating ions of particular mobility and means for directing ions to a solid substrate may be of any type know in the art, including those selected from the group consisting of direction by an electrostatic-field, direction by a magnetic-field, and combinations thereof. Means for gating and deflecting are preferably performed using electrostatic or magnetic fields, however, mechanical means may be used. Means for gating and directing are preferably performed by using electrostatic steering plates, however, other techniques well known in the art may be used, and these include direction by the application of magnetic fields also. Mechanical means for gating through the use of shutters is also possible.

The instrument and method of the present invention, in addition to its ability to selectively gate and direct analyte ions onto a substrate, can also incorporate a number of recent advances in ion mobility/mass spectrometry. For example, in U.S. Pat. No. 6,6,639,213 to Gillig et al, an improved ion mobility instrument using periodic focusing electric fields that minimize the spatial spread of the migrating ions by keeping them in a tight radius about the axis of travel is described. U.S. Pat. No. 6,6,639,213 is incorporated by reference as though fully described herein. In U.S. application Ser. No. 09/798,030 (published as U.S. Patent Application Publication 2001/0032929 A1 on Oct. 25, 2001), Fuhrer et al, disclosed an improved ion mobility instrument using combinations of periodic and hyperbolic focusing electric fields. U.S. Patent Application Publication 2001/0032929 A1 is incorporated by reference as though fully described herein. In U.S. Pat. No. 6,683,299 to Fuhrer et al, time-of-flight mass spectrometer instruments for monitoring fast processes using an interleaved timing scheme and a position sensitive detector are described. U.S. Pat. No. 6,683,299 is incorporated by reference as though fully described herein. In U.S. application Ser. No. 10/689,173 (published as U.S. Patent Application Publication 2004/0113064 A1 on Jun. 17, 2004), of Fuhrer et al, the time-of-flight mass spectrometer instruments for monitoring fast processes using an interleaved timing scheme and a position sensitive detector was supplemented with an additional fragmentation step for additional analytical information. U.S. Patent Application Publication 2004/0113064 A1 is incorporated by reference as though fully described herein. In pending U.S. application Ser. No. 10/967,715, Fuhrer et al described improvements in the fast time-of-flight instrument, including photo-fragmentation of ions, the use of multiple pixel ion detectors positioned within the mass spectrometer, and the generation and analysis of one or more spatially distinct ion beamlets. It is understood that a time of flight mass spectrometer can be used as a detector stage in place of detector 5. In pending U.S. application Ser. No. 10/969,643, Schultz et al describe improved ion mobility focusing through the use of alternating high and low electric field regions. U.S. application Ser. No. 10/969,643 is incorporated by reference as though fully described herein.

Figure 3:
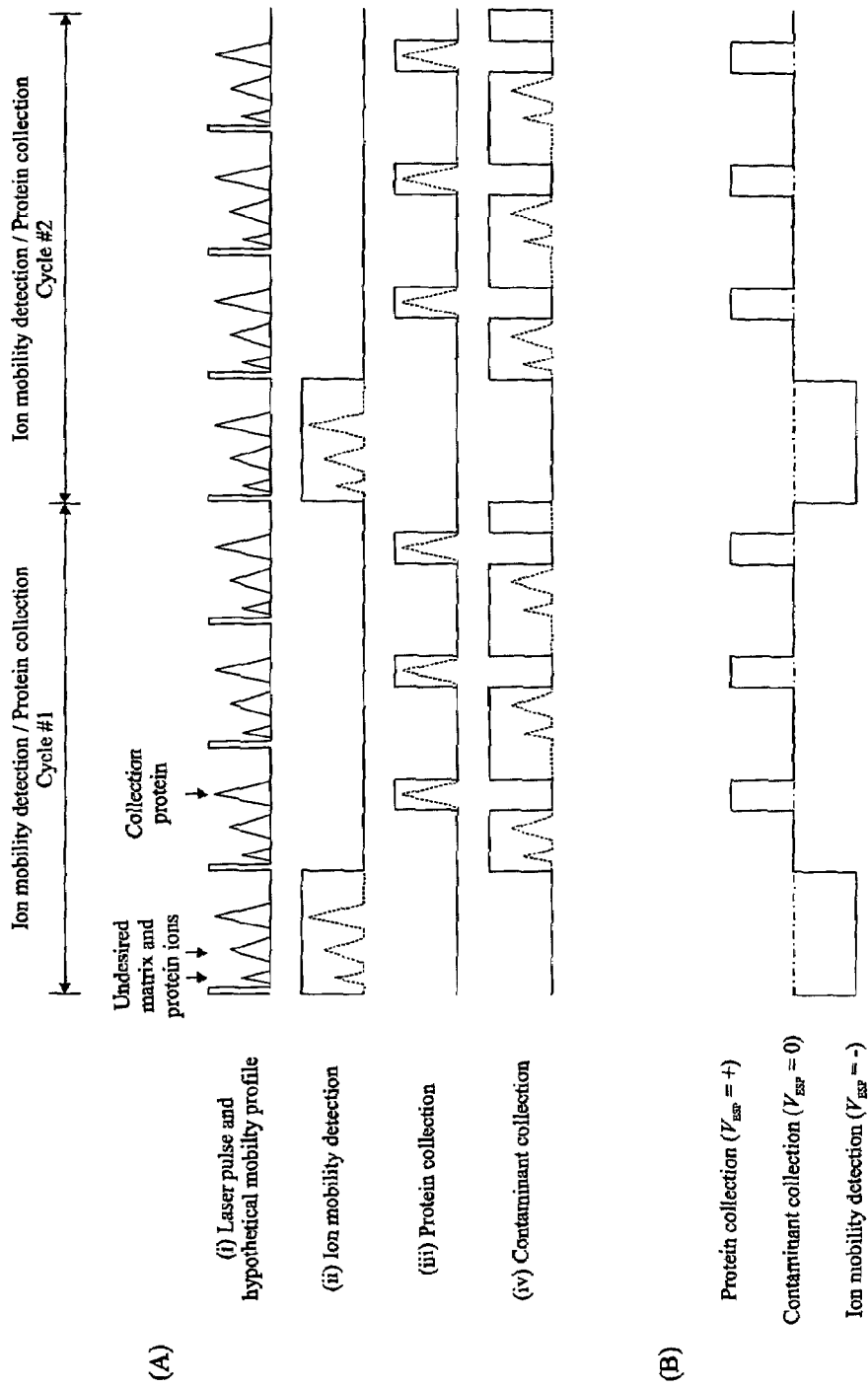
FIG. 3 is a (A) Diagram of the timing of two ion mobility detection/protein collection cycles utilizing a 75% duty cycle. (B) Schematic diagram of the relative steering plate voltages ($V_{ESP}$) for each stage of the detection/separation scheme in (A)

A representative timing diagram for the voltage applied to the electrostatic steering plates is illustrated in FIG. 3 for two cycles of ion mobility detection and peptide/protein deposition. In this example, all of the ions from the initial MALDI event are directed to the detector to determine the arrival time distribution of the ion mobility separated ions (FIG. 3A(ii)). Based on the elution time of the peptide or protein to be deposited which was determined in (ii), ions eluting at that time are then directed to the collection surface 6 for the remaining ionization events in that cycle (FIG. 3A(iii)). For elution times not corresponding to either detection or collection, no net steering is used so that undesired ions (e.g., from contaminants or matrix related ions), and neutrals are collected on a contaminant collection probe. Owing to the plane of symmetry between the collection probe and detector, the voltage applied to the electrostatic steering plates is the same in magnitude, but opposite in polarity, depending on the desired ultimate trajectory of the ions (i.e., detector or collector, FIG. 3B). By changing the magnitude of the voltage applied, the spatial position of the ion deposition can be tuned. It should be understood that the dimensions of the deflections and the distances between the detector 5, collector 6, and contaminant collection probe 16 can be very small (miniaturized).

Figure 4:
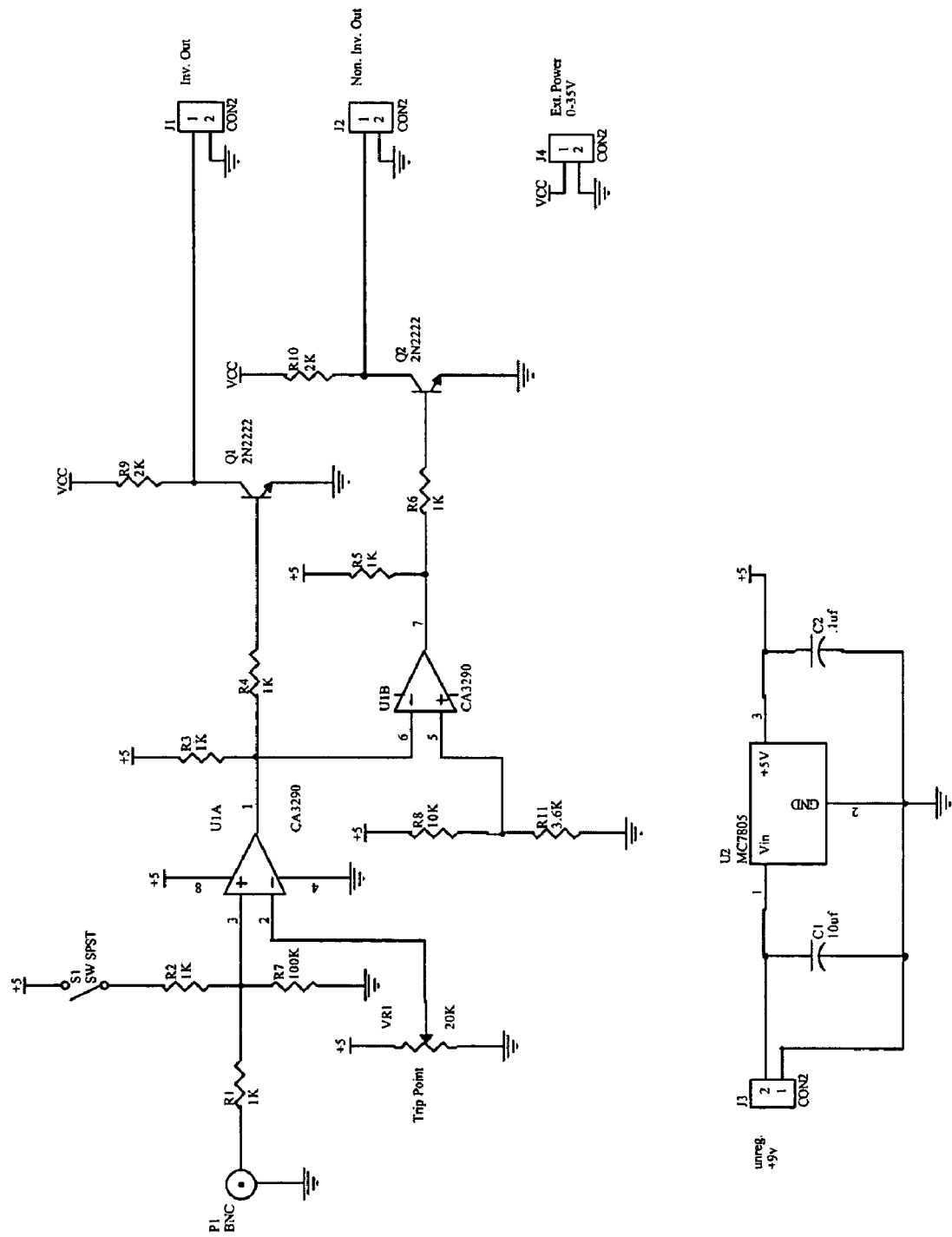
FIG. 4 is a Schematic diagram of the alternating fast-switch circuitry used to electrostatically direct ions to either the detection or collection plane.
Figure 5:
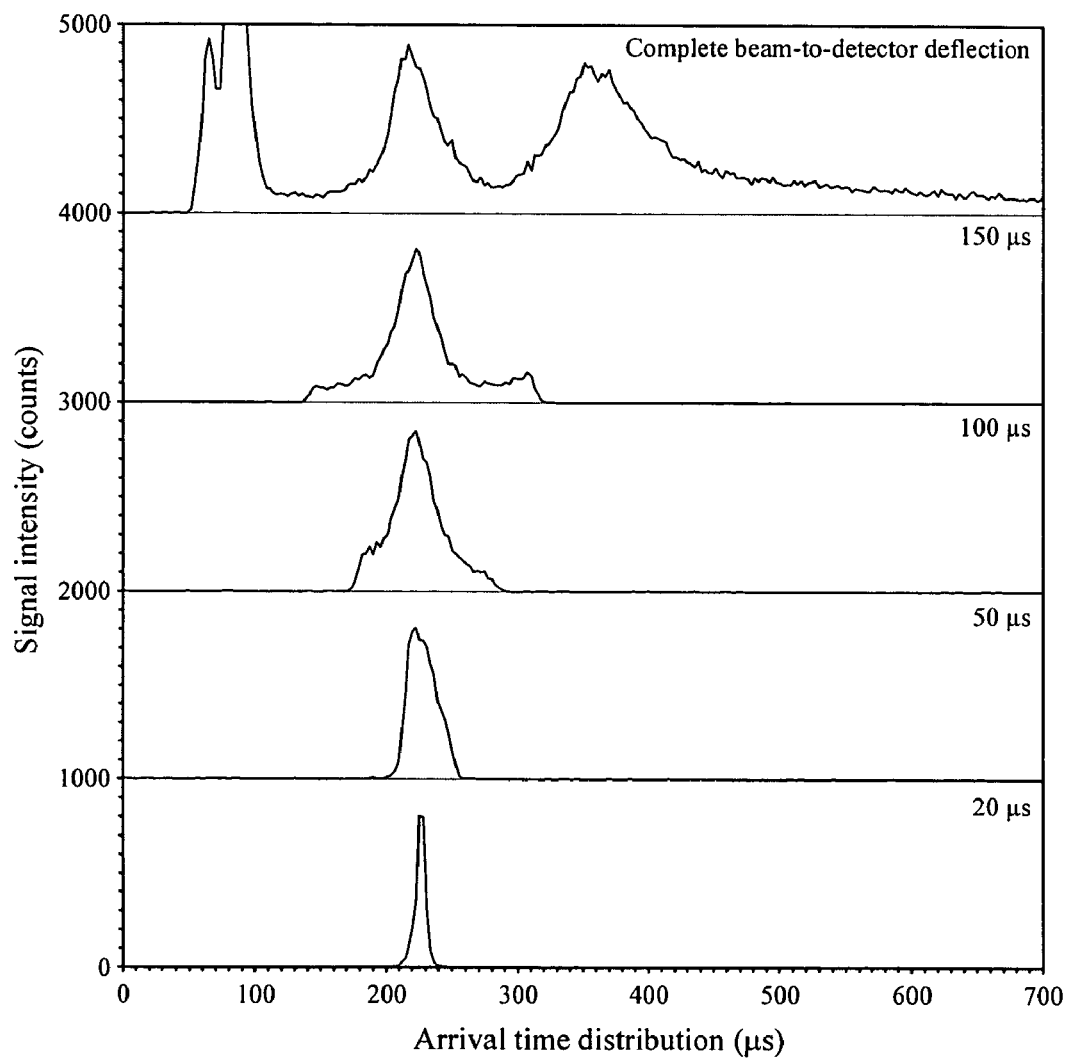
FIG. 5. is a Arrival time distribution plots illustrating the selectivity achievable with the switching circuitry. Plots illustrate (top) complete beam-to-detector deflection, and decreasing the deflected pulse from 150 to 20 μs around the peak centered at 225 μs FIG. 6. A MALDI-time-of-flight-MS spectrum of gramicidin s recovered from the collection surface after ion mobility-soft-landing deposition

In the present exemplary embodiment, steering plate voltage polarity is determined by the electronic state of fast-switching circuitry (FIG. 4). The state of the switch is changed by the application of a tunable waveform (±5 V) constructed on the basis of the timing diagram as illustrated in FIG. 3. When the inverted (−) or non-inverted (+) output state is "high" the switch delivers a voltage equal to that supplied by an external power supply (±0 to 35 V) to the inverted or non-inverted electrostatic steering plate, respectively. Concurrently, the inverted or non-inverted output in the "low" state is connected to ground. The current circuitry has a rise/fall time of ca. 1 ns and can operate up to a switching frequency of approximately 100 kHz. Arrival time distribution selectivity (i.e., mobility separated ion selectivity) by using the switching circuitry described is illustrated in FIG. 5. The top panel illustrates the arrival time distribution observed by gating all mobility-separated ions (atomic ions ablated from the steel probe tip, matrix related ions (α-cyano hydroxycinnamic acid), and the peptide gramicidin s) to the detector. In subsequent panels, the steering plates are gated to transmit ions from the peak eluting at 220 µs, but in successively more selective timing windows ranging from 150 to 20 µs. Note that owing to the symmetry of the instrument, the selected ions in FIG. 5 are directed to the surface by simply switching the electronic state of the switching circuitry. In terms of selectivity, there is little to no evidence for ions reaching the detector from rejected portions of the arrival time distribution.

Figure 6:
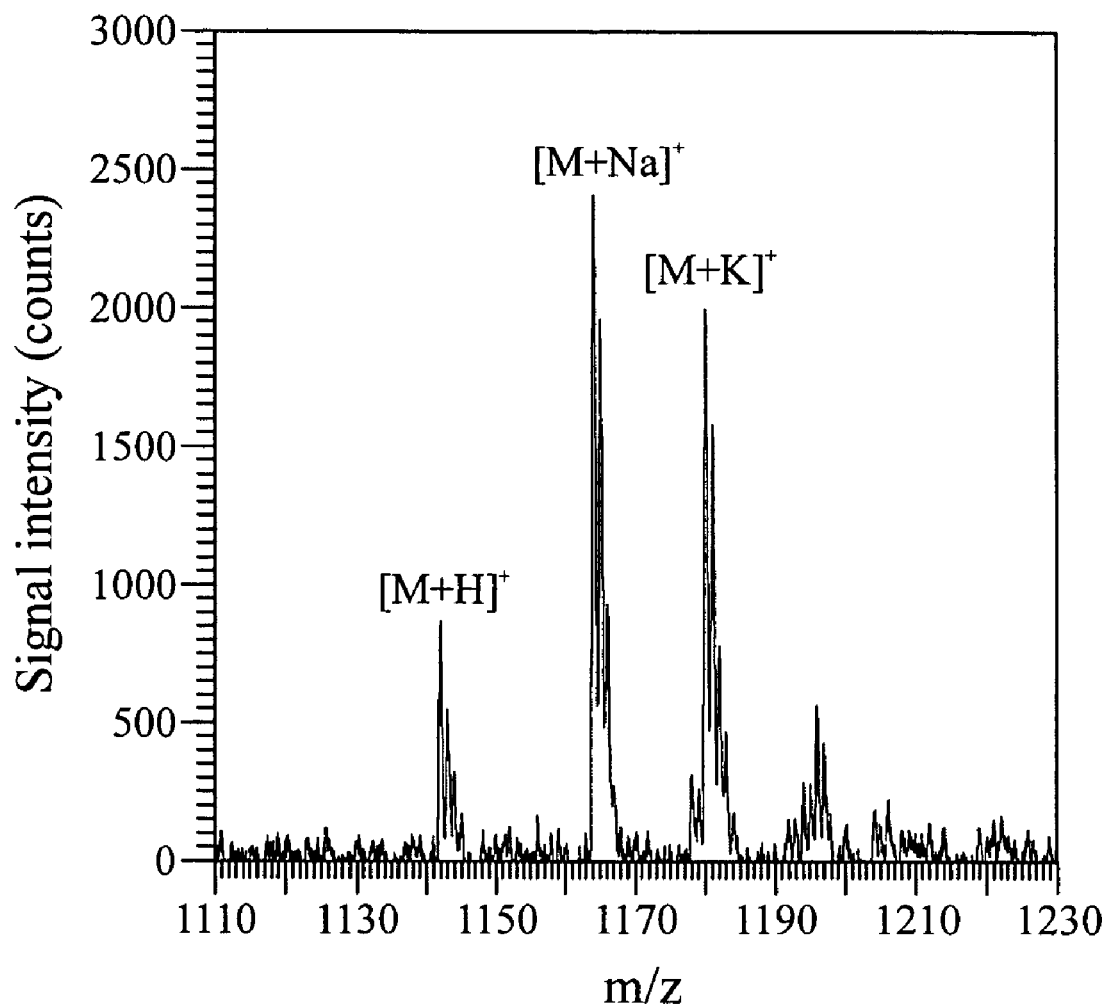

An instrument was built based upon the exemplary embodiment of the present invention for proof-of-concept experiments. The peptide gramicidin s ([PVOLF]$_2$) was soft-landed (7.5 eV kinetic energy) onto a hydrocarbon coated-stainless steel collection surface for 15 hours at a MALDI repetition rate of 30 Hz. The deposited peptide was then washed into 10 µL of deionized water, spotted onto a MALDI sample plate with a co-matrix of 2,5-dihydroxybenzoic acid, and then analyzed by MALDI-time-of-flight-MS resulting in the spectrum illustrated in FIG. 6. This spectrum clearly indicates that gramicidin s is deposited on the collection surface intact. In another embodiment, the utilization of high repetition rate MALDI (i.e., 0.5 to 10 kHz) will reduce these deposition times to several minutes.

In the present exemplary embodiment, the collection surface is positioned at a point equidistant from the steering region as that from the detector plane to said region. The collection surface may consist of a static probe, plate, or microwell plate and may be surface modified. The spatial addressability of ion deposition can be accomplished by one or more pairs of electrostatic steering plates (or other ion optical geometries). Manipulation of the direction of ion deposition can be used to pattern the deposition. In an alternate embodiment, the ion beam position remains static and the collection surface is translated relative to the ion beam via x-y micropositioners for spatial addressability. The ultimate spatial resolution of deposited peptides or proteins on the collection surface, in the present exemplary embodiment, is limited by the diameter of the differential aperture plate 12 (ca. 200 µm), but could be conservatively improved to 10 to 100 µm$^2$ spot sizes by utilizing ion optical methods well known in the art.

In alternate embodiments of the present invention (FIG. 1B), on-line analysis of the amount of analyte deposited will be accomplished by in situ analysis of the native-state fluorescence of the gas-phase ions by means of using a pulsed-laser source of UV photons for excitation 18 (e.g., 266 nm by using a frequency-quadrupled Nd:YAG laser) and measuring emission by means of an avalanche photodiode or photomultiplier tube detector 19 situated 90° with respect to the fluorescence laser propagation. In the presently-described exemplary embodiment, the focused beam of ions passes through a fluorescence interaction region 20 for non-destructive detection prior to soft-landing at the collection surface 21. Excess excitation photons and undesired ions deflected by means of the steering plates are collected at a photon/ion beam dump 22 positioned in-line with the excitation laser.

In either embodiment, the collection surface may consist of a variety of materials, for example: steel, gold, glass, H-SAM, F-SAM, glycerol, or condensed-phase materials. The collection surface can further be functionalized using alkanethiol-gold or silanization chemistries (e.g., reaction with primary amines for peptides and proteins) to immobilize and the deposited analyte. By immobilizing the analyte with covalent cross-linking agents, the deposited material can be patterned on the collection surface to generate microarrays of desired material. The present invention may alternatively be used for promoting the growth of highly ordered protein crystals from said gas-phase purified analytes. The ordering of such protein crystals may be enhanced by carefully cooling the mobility separated ions by application of RF gas phase cooling procedures and further controlling the beam energy of the thus cooled mobility separated proteins by use of carefully designed deceleration optics located in front (upstream) of the collector surface. Instrumentation and method for RF cooling are well known to those of skill in the art; see for example, U.S. Pat. No. 6,6,639,213, U.S. Patent Application Publication 2001/0032929 A1, U.S. Pat. No. 6,683,299, U.S. Patent Application Publication 2004/0113064, and U.S. application Ser. No. 10/969,643; these patents and published patent applications are incorporated by reference as though fully described herein. This crystallization may also be desirably influenced by the choice of collector surface morphology which might include, for example, an ordered single crystalline substrate. The use of a two dimensional mobility spectrometer could also be used (with or without gating techniques) for simultaneously spatially separating and depositing the entire output of the MALDI (or laser ablation) ionization process. The generation of the analyte ions is not restricted to the MALDI process. The practice of this invention would easily include the use of a pulsed or trapped output from a continuous soft ionization source. Alternatively the use of a continuous generation of the ions by, for example, electrospray ionization followed by a differential ion mobility spectrometer for selecting the desired analyte ions for deposition. One application of any of these embodiments will be to crystallize proteins or epitopes of drug binding sites of proteins so that their atomic structure can be determined by synchrotron generated X-ray diffraction techniques so that the atomic composition and geometric orientation of the drug binding site can be determined. One additional application is in drug screening which is made possible by the combination of soft ionization, mobility separation, gating and soft landing for the growth of biocrystals which contain a small molecule drug candidate already interacting with the protein which contains the targeted binding site. The growth of these single crystal proteins or peptide which containing the small molecule can thus enable the structure determination by X-ray diffraction. This allows the direct determination of whether or not the potential drug candidate reaches the binding site and if so how it interacts with the binding site. A further application is the soft landing of semiconductor or small metal particulates so that combinatorial analysis of physical properties (e.g. chemical reactivity, electron emission, catalytic activity, photoemission of electrons) can be rapidly determined.

All patents and publications referenced herein are hereby incorporated by reference. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

REFERENCES

U.S. Pat. No. 4,822,466 J. W. Rabalais and S. R. Kasi, Chemically Bonded Diamond Films and Method for Producing Same (Apr. 18, 1989).
U.S. Pat. No. 5,374,318 J. W. Rabalais and S. R. Kasi, Process for the Deposition of Diamond Films Using Low Energy, Mass-Selected Ion Beam Deposition (Dec. 20, 1994).
20010032930 K. J. Gillig and D. H. Russell, Periodic Field Focusing Ion Mobility Spectrometer (Application filed Feb. 28, 2001).
20010032929 K. Fuhrer, K. J. Gillig, M. Gonin, D. H. Russell, J. A. Schultz, Mobility Spectrometer (Application filed Feb. 28, 2001)

Foreign Patent Documents

JP2002069622 K. Koji, N. Atsushi, S. Takeshi, Soft-Landing Method for Cluster Ion Species (Aug. 3, 2002).
WO 99/38194 C. M. Whitehouse, B. A. Andrien Jr., Mass Spectrometry from Surfaces (Jul. 29, 1999).

Literature and Presentations

[1]. E. W. McDaniel and E. A. Mason, *The Mobility and Diffusion of Ions in Gases*, Wiley, New York, N.Y. (1973).
[2]. E. A. Mason and E. W. McDaniel, *Transport Properties of Ions in Gases*, John Wiley & Sons, Inc., New York, N.Y. (1988).
[3]. W. S. Barnes, D. W. Martin, and E. W. McDaniel, Mass Spectrographic Identification of the Ion Observed in Hydrogen Mobility Experiments, *Phys. Rev. Lett.* 6, 110–111 (1961).
[4]. V. Grill, J. Shen, C. Evans, and R. G. Cooks, Collisions of Ions with Surfaces at Chemically Relevant Energies: Instrumentation and Phenomena, *Rev. Sci. Instrum.* 72, 3149–3179 (2001).
[5]. M. R. Morris, D. E. Riederer Jr., B. E. Winger, R. G. Cooks, T. Ast, and C. E. D. Chidsey, Ion/Surface Collisions at Functionalized Self-Assembled Monolayer Surfaces, *Int. J. Mass Spectrom. Ion Proc.* 122, 181–217 (1992).
[6]. V. Franchetti, B. H. Solka, W. E. Baitinger, J. W. Amy, and R. G. Cooks, Soft Landing of Ions as a Means of Surface Modification, *Int. J. Mass Spectrom. Ion Phys.* 23, 29–35 (1977).
[7]. J. W. Rabalais and S. Kasi, Growth of Thin Chemically Bonded Diamondlike Films By Ion Beam Deposition, *Science* 239, 623–625 (1988).
[8]. H. Kang, S. R. Kasi, and J. W. Rabalais, Interactions of Low Energy Reactive Ions with Surfaces. I. Dose and Energy Dependence of 3–300 eV $C^+$, $O^+$, and $CO^+$ Reactions with a Ni(111) Surface, *J. Chem. Phys.* 88, 5882–5893 (1988).
[9]. S. A. Miller, H. Luo, S. J. Pachuta, and R. G. Cooks, Soft-Landing of Polyatomic Ions at Fluorinated Self-Assembled Monolayer Surfaces, *Science* 275, 1447–1450 (1997).
[10]. H. Luo, S. A. Miller, R. G. Cooks, and S. J. Pachuta, Soft Landing of Polyatomic Ions for Selective Modifica-

[11]. J. Shen, Y.-H. Yim, B. Feng, V. Grill, C. Evans, and R. G. Cooks, Soft Landing of Ions onto Self-Assembled Hydrocarbon and Fluorocarbon Monolayer Surfaces, *Int. J. Mass Spectrom.* 182/183, 423–435 (1999) and references therein.

[12]. B. Feng, D. S. Wunschel, C. D. Masselon, L. Pasa-Tolic, and R. D. Smith, Retrieval of DNA Using Soft-Landing After Mass Analysis by ESI-FTICR for Enzymatic Manipulation, *J. Am. Chem. Soc.* 121, 8961–8962 (1999).

[13]. B. Gologan, Z. Takats, T. Blake, Z. Ouyang, V. J. Davisson, and R. G. Cooks, Self-Assembled Monolayers as Substrates for Laser Desorption: Analysis of Soft-Landed Proteins, presented at the 51st American Society for Mass Spectrometry Conference, Montreal, Canada, June 2003.

[14]. Z. Takats, Z. Ouyang, B. Gologan, T. Blake, A. J. Guymon, V. J. Davisson, and R. G. Cooks, Protein Microarrays by Ion Soft-Landing, presented at the 51st American Society for Mass Spectrometry Conference, Montreal, Canada, June 2003.

T. A. Blake, Z. Ouyang, A. J. Guymon, S. Kothari, Z. Takats, B. Gologan, and R. G. Cooks, A Microarray Fabrication System Using Ion Soft-Landing from a Linear Ion Trap Mass Analyzer, presented at the 51st American Society for Mass Spectrometry Conference, Montreal, Canada, June 2003.

What is claimed is:

1. An apparatus for detecting and selectively depositing gas-phase ions onto a surface, comprising:
   an ion source for generating ions;
   means for separating the generated ions, said means for separating being fluidly coupled to said ion source;
   means for selectively gating said ions based on their mobilities and means for directing said ions to a substrate, wherein said means for selectively gating comprises gating by application of electrostatic fields, magnetic fields or both electrostatic and magnetic fields, wherein said application of said fields uses time profiles comprising discrete timing windows, and wherein said means for selectively gating and said means for directing are fluidly coupled to said means for separating; and,
   an ion detector fluidly coupled to said means for separating.

2. The apparatus of claim 1, wherein said ion source is selected from the group consisting of atmospheric pressure MALDI, infrared MALDI, LDI, electrospray, nanospray, photoionization, multiphoton ionization, resonance ionization, thermal ionization, surface ionization, electric field ionization, chemical ionization, atmospheric pressure chemical ionization, radioactive ionization, discharge ionization, and any combination thereof.

3. The apparatus of claim 1, wherein said means for separating comprises an ion mobility cell or a mass spectrometer or both.

4. The apparatus of claim 3, wherein said means for separating comprises an ion mobility cell.

5. The apparatus of claim 4, wherein said ion mobility cell applies electric fields selected from the group consisting of uniform electrostatic fields, periodic-focusing electrostatic fields, and any combinations thereof.

6. The apparatus of claim 1, wherein ions are further separated by unreactive and/or reactive collisions with species selected from the group consisting of helium, neon, argon, krypton, xenon, nitrogen, oxygen, methane, carbon dioxide, water, methanol, methyl fluoride, deuterated analogs thereof, tritiated analogs thereof, and any combination thereof.

7. The apparatus of claim 1, wherein the means for selectively gating ions based on their mobilities and directing them to a solid substrate comprises directing ions by a technique selected from the group consisting of direction by an electrostatic-field, direction by a magnetic-field, and a combination of direction by an electrostatic-field and direction by a magnetic-field.

8. The apparatus of claim 1 wherein said means for selectively gating and said means for directing are the same.

9. The apparatus of claim 8, wherein said means comprises an electrostatic steering plate.

10. The apparatus of claim 1, wherein the apparatus gates and directs ions to a solid or condensed-phase surface at energies of 0 to 10 eV.

11. The apparatus of claim 1, wherein the apparatus gates and directs ions to a solid or condensed-phase surface at energies of 10 to 100 eV.

12. The apparatus of claim 1, wherein the apparatus gates and directs ions to a solid or condensed-phase surface at energies of 100 to 1000 eV.

13. The apparatus of claim 1, wherein the apparatus gates and directs ions to spatially distinct regions of a surface comprising a material selected from the group consisting of steel, gold, glass, self-assembled monolayer(s), nitrocellulose, condensed-phase substrates, chemically functional moieties, chemically reactive moieties, biologically active species, and combinations, patterns and layers thereof.

14. The apparatus of claim 1, further comprising an RF cooling apparatus.

15. The apparatus of claim 1, further comprising deceleration optics upstream of said substrate.

16. An apparatus for detecting and selectively depositing gas-phase ions onto a surface, comprising:
   an ion source for generating ions;
   a two dimensional ion mobility drift cell fluidly coupled to said ion source;
   means for directing said ions to a substrate, said means for directing comprises selectively gating said ions by application of electrostatic fields, magnetic fields or both electrostatic and magnetic fields, wherein said application of said fields uses time profiles comprising discrete timing windows, said means for directing being fluidly coupled to said ion mobility drift cell.

17. A method for analyzing and selectively depositing gas phase ions comprising:
   generating ions from an ion source;
   separating said ions;
   detecting said ions; and,
   selectively gating and directing said ions onto a substrate, said step of selectively gating comprises selectively gating said ions by application of electrostatic fields, magnetic fields or both electrostatic and magnetic fields, wherein said application of said fields uses time profiles comprising discrete timing windows.

18. The method of claim 17, wherein said step of selectively gating and directing comprises depositing said ions onto a substrate in a spatially addressable manner by patterning ions onto a solid substrate, patterning ions onto a condensed-phase substrate, or a combination of patterning ions onto a solid substrate and patterning ions onto a condensed-phase substrate.

19. The method of claim 18, wherein the ions to be patterned comprise ions of species selected from the group consisting of amino acids, polyamino acids, nucleotides, polynucleotides, antibodies, antibody antigens, carbohydrates, polycarbohydrates, biomolecules, ligands, mimics, aptamers, derivatives thereof, assemblies thereof, complexes thereof, and any combination thereof.

20. The method of claim 17, wherein the ions comprise proteins or peptides or both.

21. The method of claim 17, wherein the ions comprise small molecules interacting with proteins or peptides or both proteins and peptides.

22. The method of claim 17, wherein said step of directing promotes the growth of ordered crystals.

23. The method of claim 18, wherein said step of patterning comprises patterning ions with a molecular weight less than 100000 amu.

24. The method of claim 18, wherein said step of patterning comprises patterning ions with a molecular weight less than 10000 amu.

25. The method of claim 18, wherein said step of patterning comprises patterning ions with a molecular weight less than 1000 amu.

26. The method of claim 18, wherein said step of patterning comprises patterning ions with a molecular weight less than 500 amu.

27. The method of claim 18, wherein said step of patterning comprises patterning ions with a molecular weight greater than 100000 amu.

* * * * *